(12) United States Patent
Zhou

(10) Patent No.: US 11,680,235 B2
(45) Date of Patent: Jun. 20, 2023

(54) CELL SHEET TRANSFER DEVICE AND CELL SHEET PROCESSING EQUIPMENT

(71) Applicant: BOE TECHNOLOGY GROUP CO., LTD., Beijing (CN)

(72) Inventor: Shi Zhou, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 206 days.

(21) Appl. No.: 16/759,127

(22) PCT Filed: Sep. 27, 2018

(86) PCT No.: PCT/CN2018/107840
§ 371 (c)(1),
(2) Date: Apr. 24, 2020

(87) PCT Pub. No.: WO2019/148864
PCT Pub. Date: Aug. 8, 2019

(65) Prior Publication Data
US 2021/0179990 A1    Jun. 17, 2021

(30) Foreign Application Priority Data
Jan. 30, 2018  (CN) .......................... 201810091558.3

(51) Int. Cl.
  *C12M 3/00*  (2006.01)
  *B01L 1/00*  (2006.01)
  *C12M 1/12*  (2006.01)
  *C12M 1/04*  (2006.01)
  *C12M 1/26*  (2006.01)

(52) U.S. Cl.
  CPC ............ *C12M 23/06* (2013.01); *C12M 23/24* (2013.01); *C12M 25/02* (2013.01); *C12M 33/04* (2013.01); *C12M 33/14* (2013.01)

(58) Field of Classification Search
  CPC .............................. C12M 33/04; C12M 23/06
  See application file for complete search history.

(56) References Cited

U.S. PATENT DOCUMENTS

| 5,208,161 A  | * | 5/1993 | Saunders | B01D 61/142 |
| | | | | 210/232 |
| 10,357,767 B1 | * | 7/2019 | Sternick | B01L 3/0275 |
| 2005/0106718 A1 | * | 5/2005 | Balasubramanian | G01N 1/02 |
| | | | | 435/309.1 |
| 2006/0051735 A1 | * | 3/2006 | Fuhr | G01N 15/14 |
| | | | | 435/4 |
| 2011/0124037 A1 | * | 5/2011 | Backhaus | C12M 41/06 |
| | | | | 435/30 |

(Continued)

FOREIGN PATENT DOCUMENTS

| CN | 1761743 A | 4/2006 |
| CN | 101031636 A | 9/2007 |

(Continued)

*Primary Examiner* — Nathan A Bowers
(74) *Attorney, Agent, or Firm* — The Webb Law Firm

(57) ABSTRACT

A cell sheet transfer device and a cell sheet processing equipment. The cell sheet transfer device includes a first tubular body; a second tubular body at one end of the first tubular body and connected thereto; and a cell shovel at the end of the first tubular body and on one side of the second tubular body. A free end of the cell shovel is beyond a free end of the second shovel body.

15 Claims, 7 Drawing Sheets

(56) References Cited

U.S. PATENT DOCUMENTS

2013/0205922 A1\* 8/2013 Leventhal ................. B01L 3/18
73/864.01

FOREIGN PATENT DOCUMENTS

| CN | 102586091 A | 7/2012 |
|----|-------------|--------|
| CN | 205216872 U | 5/2016 |
| CN | 205528774 U | 8/2016 |
| CN | 106479876 A | 3/2017 |
| CN | 206509001 U | 9/2017 |
| CN | 107418998 A | 12/2017 |
| CN | 107560980 A | 1/2018 |
| CN | 107603870 A | 1/2018 |
| EP | 1605038 A1 | 12/2005 |
| EP | 1801199 A1 | 6/2007 |
| EP | 3202894 A1 | 8/2017 |

\* cited by examiner

CELL SHEET TRANSFER DEVICE AND CELL SHEET PROCESSING EQUIPMENT

CROSS-REFERENCE TO RELATED APPLICATIONS

This application is the United States national phase of International Application No. PCT/CN2018/107840 filed Sep. 27, 2018, and claims priority to Chinese Patent Application No. 201810091558.3, filed on Jan. 30, 2018, the disclosure of which is hereby incorporated by reference in its entirety.

TECHNICAL FIELD

The disclosure relates to the field of cell sheet processing, in particular to a cell sheet transfer device and cell sheet processing equipment.

BACKGROUND

Cell sheet (Cell membrane) has been a hotspot of research in the field of tissue engineering in recent years. The cultured cell sheet is useful for treating diseases related to skin, cornea, heart, periodontal and other related diseases.

SUMMARY

According to a first aspect of embodiments of the present disclosure, there is provided a cell sheet transfer device comprising: a first tubular body; a second tubular body disposed at an end of the first tubular body and communicating with the first tubular body; and a cell shovel disposed at the end of the first tubular body and disposed on one side of the second tubular body, wherein a free end of the cell shovel exceeds a free end of the second tubular body.

In some embodiments, the cell sheet transfer device further comprises: a filter membrane disposed in the first tubular body.

In some embodiments, the filter membrane is a waterproof and air-permeable membrane.

In some embodiments, the above transfer device further comprises: a filter membrane holder disposed in the first tubular and configured to secure the filter membrane.

In some embodiments, a cross-sectional area of the second tubular body increases gradually in a direction from a connection end of the second tubular body and the first tubular body toward the free end of the second tubular body.

In some embodiments, the first tubular body comprises a bending section.

In some embodiments, a bending angle of the bending section is from 30 degrees to 60 degrees.

In some embodiments, the above transfer device further comprises: a pressure regulator disposed on the first tubular body and configured to regulate pressure inside the first tubular body.

In some embodiments, a material of the first tubular body and a material of the second tubular body are high histocompatibility materials.

In some embodiments, the high histocompatibility material comprises at least one of polyethylene, polypropylene, polyethylene glycol, polystyrene, nylon, polyacetal, polycarbonate, polyvinyl alcohol, polyethyleneimine, polysulfone, polylactic acid, polymethacrylate, polyurethane, glass, ceramic, or dextran.

According to a second aspect of embodiments of the present disclosure, there is provided a cell sheet processing apparatus comprising a cell sheet transfer device, the cell sheet transfer device comprises: a first tubular body; a second tubular body disposed at an end of the first tubular body and communicating with the first tubular body; and a cell shovel disposed at the end of the first tubular body and disposed on one side of the second tubular body, wherein a free end of the cell shovel exceeds a free end of the second tubular body.

In some embodiments, the processing device further comprises: a cell sheet suction device configured to suction a cell sheet.

In some embodiments, the cell sheet suction device comprises: a connection tube; and a suction member disposed at an end of the connection tube and configured to communicate with the connecting tube to suction the cell sheet.

In some embodiments, a cross-sectional area of the suction member increases gradually in a direction from a connection end of the suction member and the connection tube to a free end of the suction member.

In some embodiments, the cell sheet suction device further comprises: a pressure regulator disposed on the connection tube and configured to regulate the pressure inside the connection tube.

In some embodiments, the cell sheet suction device further comprises a filter membrane disposed in the suction member.

In some embodiments, the cell sheet suction device further comprises: a suction plate disposed on one side of the free end of the filter membrane close to the suction member.

In some embodiments, the suction plate is provided with through holes.

In some embodiments, the processing device further comprises: a first pressure source configured to communicate with the first tubular body of the cell sheet transfer device through a first pipeline to make the cell sheet transfer device blow up the cell sheet; a second pressure source configured to communicate with the connection tube of the cell sheet suction device through a second pipeline to make the cell sheet suction device to suction the cell sheet.

In some embodiments, the processing device further comprises: a first three-way valve disposed on the first pipeline; and a second three-way valve disposed on the second pipeline.

Other features of the present disclosure and advantages thereof will become apparent from the following detailed description of exemplary embodiments thereof, which proceeds with reference to the accompanying drawings.

BRIEF DESCRIPTION OF THE DRAWINGS

The accompanying drawings, which are incorporated in and constitute a part of this specification, illustrate embodiments of the disclosure and together with the description, serve to explain the principles of the disclosure.

The present disclosure may be understood more clearly from the following detailed description with reference to the accompanying drawings, in which.

It should be understood that the dimensions of the various parts shown in the drawings are not drawn according to the actual proportional relationship. Further, the same or similar reference numerals denote the same or similar components.

DETAILED DESCRIPTION

Figure 1:
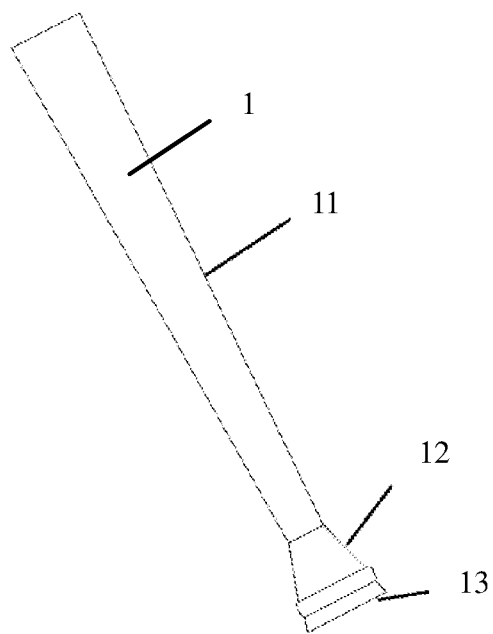
FIG. 1 is a schematic structural view of a cell sheet transfer device according to one embodiment of the present disclosure.

Various exemplary embodiments of the present disclosure will now be described in detail with reference to the accompanying drawings. The description of the exemplary embodiments is merely illustrative and is in no way intended to limit the disclosure, its application, or uses. The present disclosure may be embodied in many different forms and is not limited to the embodiments described herein. These embodiments are provided so that this disclosure will be thorough and complete, and will fully convey the scope of the disclosure to those skilled in the art. It should be noted that: the relative arrangement of parts and steps, the composition of materials and values set forth in these embodiments are to be construed as illustrative only and not as limiting unless otherwise specifically stated.

The use of "first," "second," and similar words in this disclosure is not intended to indicate any order, quantity, or importance, but rather is used to distinguish one element from another. The word "comprising" or "including", and the like, means that the element preceding the word comprises the element listed after the word, and does not exclude the possibility that other elements may also be included. "Upper", "lower", "left", "right" and the like are used only to indicate relative positional relationships, and when the absolute position of the object being described is changed, the relative positional relationships may also be changed accordingly.

In the present disclosure, when a particular device is described as being located between a first device and a second device, intervening devices may or may not be present between the particular device and the first or second device. When a particular device is described as being coupled to another device, it may be directly coupled to the other device without intervening devices or may not be directly coupled to the other device with intervening devices.

All terms (including technical or scientific terms) used herein have the same meaning as commonly understood by one of ordinary skill in the art to which this disclosure belongs unless specifically defined otherwise. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In the present disclosure, a free end includes an end of the device not connected to other components, for example, not connected to other devices in the extending direction of the device. On the other hand, an end of the device connected or partially connected to other devices is a connection end.

In the present disclosure, the matrix layer includes a culture matrix carrying a cell sheet and a carrying material layer of the cell sheet, for example, a material layer formed of at least one temperature sensitive material among poly N-isopropylacrylamide (PIPAAm), a complex of the PIPAAm and methacrylic acid, lysine short peptide A6K, and the like. Through temperature adjustment, under the condition that the temperature sensed by the temperature sensitive material of the matrix layer reaches a specific condition, for example, when the temperature rises/falls to a specific temperature, the cell sheet is changed from a state of being tightly attached to the temperature sensitive material to a state of being easy to strip, so that the cell sheet is convenient to be harvested and collected.

Techniques, methods, and apparatus known to one of ordinary skill in the relevant art may not be discussed in detail but are intended to be part of the specification where appropriate.

The cell sheet may be damaged during the transfer process, which may affect subsequent application. To at least partially solve this problem, the present disclosure proposes a structure of a cell sheet transfer device that can reduce the risk of damaging the cell sheet during the transfer process. The structure of the cell sheet transfer device according to some embodiments disclosed herein will be described in detail below with reference to the accompanying drawings.

FIG. 1 is a schematic structural view of a cell sheet transfer device according to one embodiment of the present disclosure.

As shown in FIG. 1, the cell sheet transfer device 1 comprises a first tubular body 11, a second tubular body 12, and a cell shovel 13. The second tubular body 12 and the cell shovel 13 are disposed at an end of the first tubular body 11, and the second tubular body 12 communicates with the first tubular body 11.

In some embodiments, when the cell sheet needs to be collected, the cell sheet and a carrying material are converted into an easily detached state through a temperature reduction treatment. Air is blown through the first tubular body 11 and the second tubular body 12 to blow up the cell sheet. The cell sheet is shoveled up by the cell shovel 13. Aspiration is performed through the first tubular body 11 and the second tubular body 12 to adsorb the cell sheet.

The above is merely illustrative of one application of the cell sheet transfer device provided in the embodiments of the present disclosure, and can be used in other applications requiring separation of the cell sheet.

In some embodiments, the second tubular body 12 and the cell shovel 13 are disposed at the end of the first tubular 11 in a stacked manner. In other embodiments, the second tubular body 12 and the cell shovel 13 are disposed at the end of the first tubular 11 in a spaced manner. For example, a connection end of the cell shovel 13 is connected to an outer side wall of the first tubular body 11 or the second tubular body 12, or to a connection end of the first tubular body 11.

In some embodiments, a free end of the second tubular body 12 can be shaped as a right rectangle, a rounded rectangle, or other suitable shape to facilitate operations of blowing and suctioning.

In some embodiments, a cross-sectional area of the second tubular body increases gradually in a direction from a connection end of the second tubular body 12 and the first tubular body 11 toward the free end of the second tubular body 12, as shown in FIG. 1.

In some embodiments, the volume of the first tubular body 11 can be from 100 microliters to 1000 microliters.

By adopting the structure, the cell sheet can be blown up more easily, meanwhile, the contact area between the cell sheet and the second tubular body can be increased, the cell sheet can be adsorbed more easily.

Figure 2:
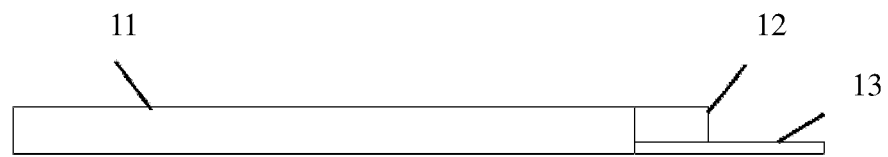
FIG. 2 is a schematic plane structural view of a cell sheet transfer device according to one embodiment of the present disclosure.

FIG. 2 is a schematic plane structural view of a cell sheet transfer device according to one embodiment of the present disclosure.

As shown in FIG. 2, the cell shovel 13 is disposed at one side of the second tubular body 12, and a free end of the cell shovel 13 extends a free end of the second tubular body 12. Because the cell shovel 13 extends longer relative to the second tubular body 12, the second tubular body 12 can avoid damaging the cell sheet when the cell shovel 13 is used for carrying out cell sheet stripping operation.

In the cell sheet transfer device provided by the above embodiment of the present disclosure, the second tubular body and the cell shovel are disposed at the end of the first tubular body, the cell sheet transfer device is used to strip the cell sheet, can absorb the cell sheet by the operations of blowing and sucking, thereby effectively avoiding the damage of the cell sheet in the transferring process.

In some embodiments, a material of the first tubular body 11 and a material of the second tubular body 12 are materials with high histocompatibility with the cell sheet. By using the high histocompatibility material, the cell sheet transfer device will not affect the cell sheet when suctioning the cell sheet.

For example, the high histocompatibility material comprises at least one of polyethylene, polypropylene, polyethylene glycol, polystyrene, nylon, polyacetal, polycarbonate, polyvinyl alcohol, polyethyleneimine, polysulfone, polylactic acid, polymethacrylate, polyurethane, glass, ceramic, or dextran.

Figure 3:
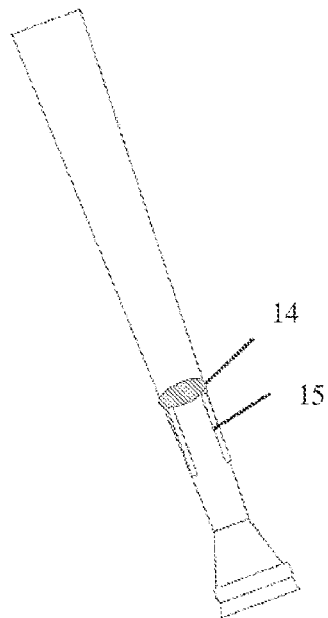
FIG. 3 is a schematic structural view of a cell sheet transfer device according to another embodiment of the present disclosure.

FIG. 3 is a schematic diagram of a cell sheet transfer device according to another embodiment of the present disclosure. In contrast to the embodiment shown in FIG. 1 and FIG. 2, in the embodiment shown in FIG. 3, the cell sheet transfer device further comprises a filter membrane 14 disposed in the first tubular body 11. By disposing the filter membrane 14, liquid is prevented from entering the upper part of the first tubular body 11, and the cell sheet is prevented from being contaminated.

In some embodiments, the filter membrane 14 is a waterproof and air-permeable membrane or other suitable membrane that prevents liquid from entering the upper part of the first tubular body while not blocking the flow of air.

In some embodiments, the waterproof and air-permeable membrane may be a PU membrane (polyurethane), TPU membrane (thermoplastic polyurethane), EPTFE membrane (expanded polytetrafluoroethylene), or the like.

In some embodiments, the filter membrane 14 is disposed in the first tubular body in a manner perpendicular to the direction of extension of the first tubular 11.

For example, the filter membrane 14 may be formed inside the first tubular body 11 by integral molding, or the filter membrane 14 may be fixed by adhesion, insertion, or the like.

In some embodiments, as shown in FIG. 3, a filter membrane holder 15 is disposed in the first tubular body 11 to secure the filter membrane 14. For example, the number of filter membrane holders 15 is from 2 to 4.

Figure 4:
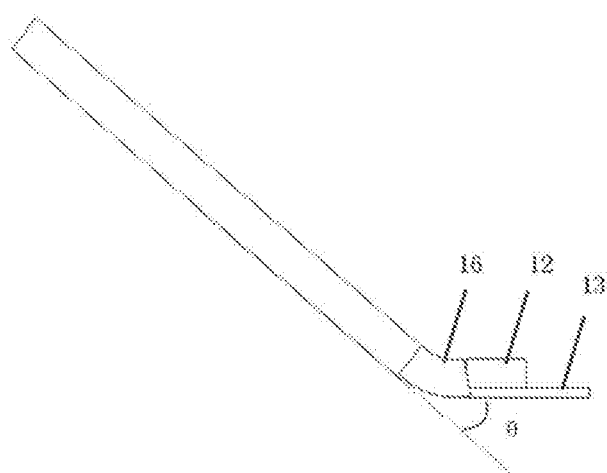
FIG. 4 is a schematic structural view of a cell sheet transfer device according to still another embodiment of the present disclosure.

FIG. 4 is a schematic diagram of a cell sheet transfer device according to still another embodiment of the present disclosure.

As shown in FIG. 4, the first tubular body 11 includes a bending section 16. By providing the bending section 16, it is convenient to provide a proper stripping angle for the user to prevent contamination due to the first tubular body 11 being excessively adhered to the culture medium or the culture solution.

In some embodiments, the bending section 16 is disposed at a lower part of the first tubular body 11, as shown in FIG. 4. The bending section may also be disposed in other locations of the first tubular body 11 as needed.

For example, the bending section 16 may be a circular arc and the bending angle θ(arc) is from 30 degrees to 60 degrees.

Figure 5:
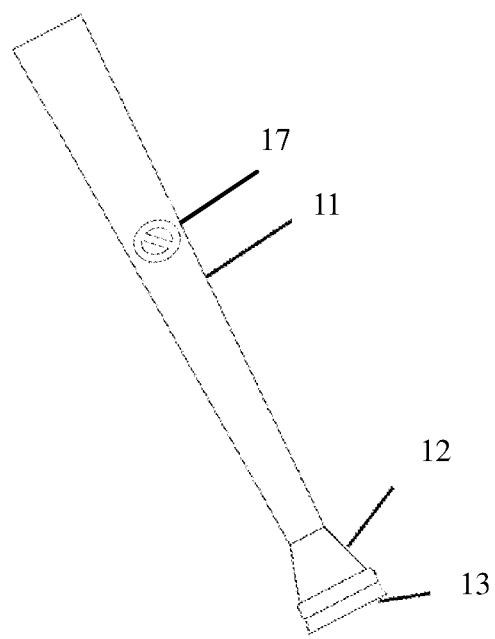
FIG. 5 is a schematic structural view of a cell sheet transfer device according to still another embodiment of the present disclosure.

FIG. 5 is a schematic structural diagram of a cell sheet transfer device according to still another embodiment of the present disclosure. As shown in FIG. 5, a pressure regulator 17 is disposed on the first tubular body 11. By providing the pressure regulator 17, the pressure inside the first tubular body 11 can be adjusted.

In some embodiments, the pressure regulator 17 is an air valve or other device capable of regulating the amount of pressure within the tubular body.

Figure 6:
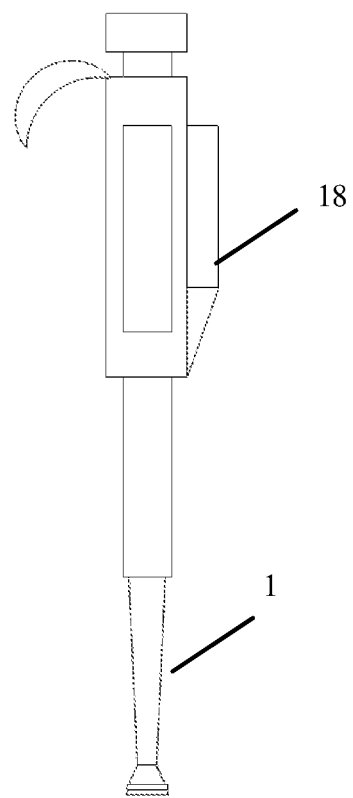
FIG. 6 is a schematic structural view of a cell sheet transfer device according to still another embodiment of the present disclosure.

FIG. 6 is a schematic structural diagram of a cell sheet transfer device according to still further embodiments of the present disclosure. As shown in FIG. 6, the cell sheet transfer device 1 may be used in cooperation with a pipette 18 to perform the operations of blowing and adsorbing the cell sheet. Of course, the cell sheet transfer device 1 may be used in combination with other suitable equipment to perform the aspiration operation.

Figure 7:
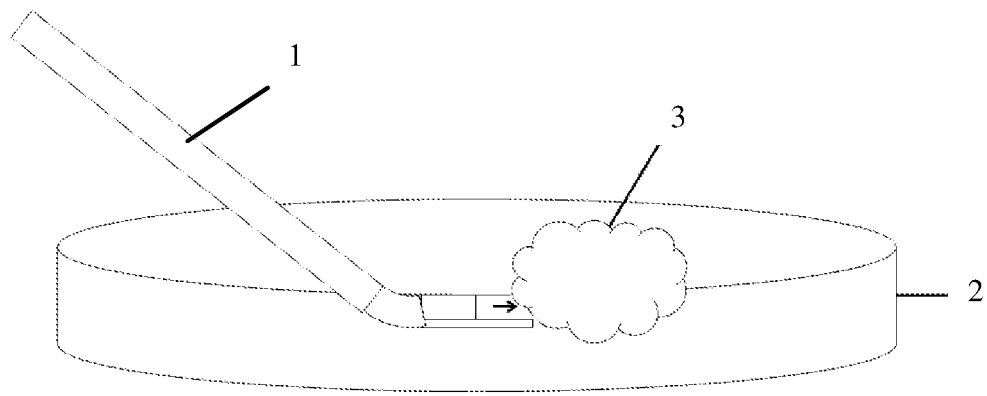
FIG. 7 is a schematic structural view of a cell sheet processing apparatus according to one embodiment of the present disclosure.

FIG. 7 is a schematic structural view of a cell sheet processing apparatus according to one embodiment of the present disclosure. As shown in FIG. 7, the cell sheet processing apparatus includes the cell sheet transfer device 1 according to any one of the above embodiments.

For example, the cell sheet 3 is stripped from the matrix layer in the culture dish by a shoveling and/or blowing operation using the cell sheet transfer device 1, and then the cell sheet maybe sucked into the tubular body of the cell sheet transfer device 1 by the negative pressure formed in the tubular body of the cell sheet transfer device 1 to transfer the cell sheet.

Figure 8:
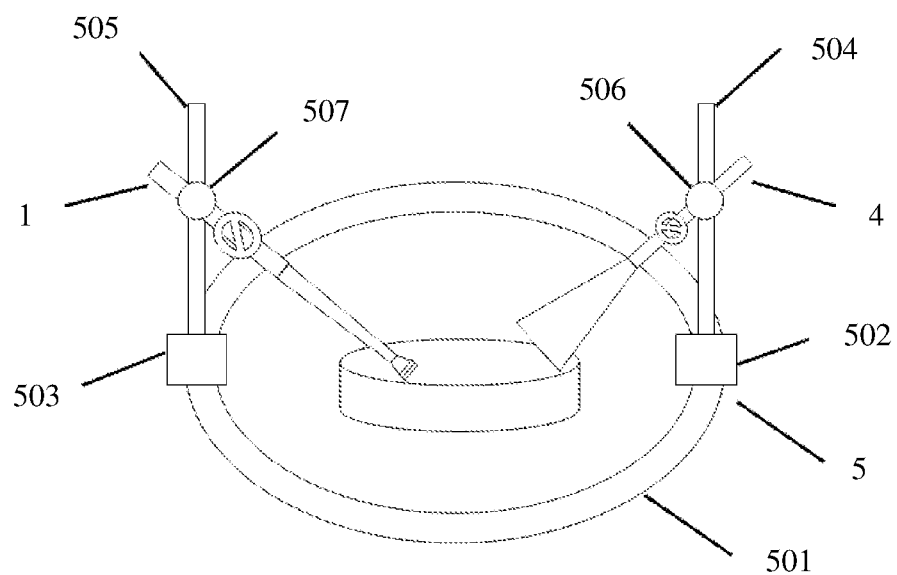
FIG. 8 is a schematic structural view of a cell sheet processing apparatus according to another embodiment of the present disclosure.

FIG. 8 is a schematic structural view of a cell sheet processing apparatus according to another embodiment of the present disclosure.

For the convenience of operation, the stripping operation and the suction operation may be performed by different devices. As shown in FIG. 8, in the cell sheet processing apparatus, the cell sheet transfer device 1 is used to strip the cell sheet, and the cell sheet suction device 4 is used to suction the cell sheet.

In some embodiments, as shown in FIG. 8, the cell sheet processing apparatus further comprises a base 5 for supporting and securing the cell sheet transfer device 1 and the cell sheet suction device 4.

In some embodiments, the base 5 comprises a track 501 such as a ring, on which a first slider 502 and a second slider 503 are disposed. A first bracket 504 is disposed on the first slider 502, and a second bracket 505 is disposed on the second slider 503. A first connecting rod 506 is disposed on the first bracket 504, the first connecting rod 506 can slide along the first bracket 504, and the first connecting member 506 is detachably connected with the cell sheet transfer device 1. A second connecting member 507 is disposed on the second bracket 505, the second connecting member 507 can slide along the second bracket 505, and the second connecting member 507 is detachably connected with the cell sheet suction device 4.

Thus, the user can easily adjust the positions of the cell sheet transfer device 1 and the cell sheet suction device 4 as needed.

Figure 9:
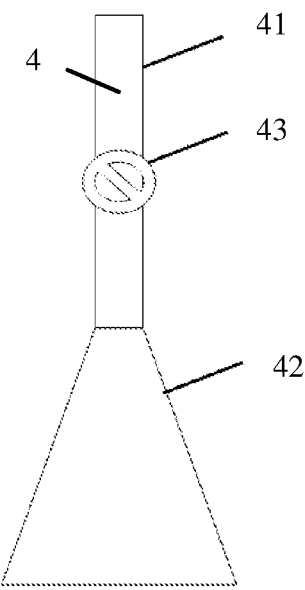
FIG. 9 is a schematic structural view of a cell sheet suction device according to one embodiment of the present disclosure.

FIG. 9 is a schematic structural diagram of a cell sheet suction device according to one embodiment of the present disclosure. As shown in FIG. 9, the cell sheet suction device 4 includes a connection tube 41, an suction member 42 at an end of the connection tube 41, the suction member 42 communicating with the connection tube 41 to suction the cell sheet when the connection tube 41 has a negative pressure.

In some embodiments, as shown in FIG. 9, a cross-sectional area of the suction member 42 increases gradually in a direction from a connection end of the suction member 42 and the connection tube 41 to a free end of the suction member 42. With this structure, the contact area between the cell sheet and the suction member 42 can be increased, and the cell sheet can be suctioned more easily.

In some embodiments, as shown in FIG. 9, the cell sheet suction device 4 further includes a pressure regulator 43 disposed on the connection tube 41 to regulate pressure in the connection tube 41.

For example, the pressure regulator 43 is a gas valve or other device capable of regulating the pressure in the connecting tube.

Figure 10:
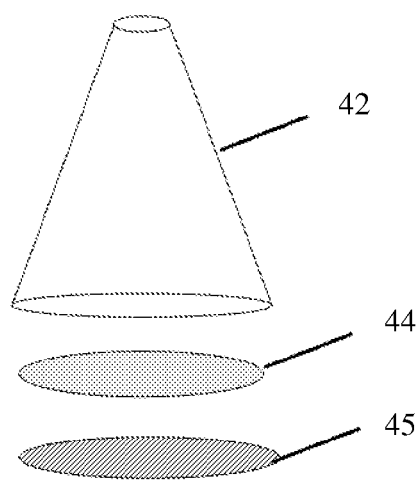
FIG. 10 is a schematic structural view of a cell sheet suction device according to another embodiment of the present disclosure.

FIG. 10 is a schematic structural view of the structure of a cell sheet suction device according to another embodiment of the present disclosure. As shown in FIG. 10, a filter membrane 44 is disposed in the suction member 42 to prevent liquid from entering the connection tube 41, and the cell sheet is prevented from being contaminated.

In some embodiments, the filter membrane 44 is a waterproof and air-permeable membrane or other suitable membrane that prevents liquid from entering the connection tube while not blocking the flow of air.

In some embodiments, as shown in FIG. 10, a suction plate 45 is disposed in the suction member 42 to suction the cell sheet.

Figure 11:
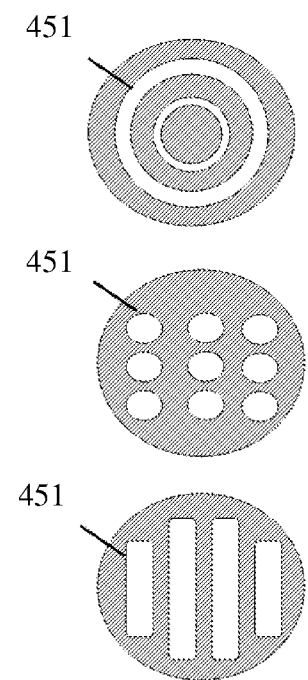
FIG. 11 is a schematic structural view of a cell sheet suction device according to still another embodiment of the present disclosure.

FIG. 11 is a schematic structural diagram of a cell sheet suction device according to still another embodiment of the present disclosure. As shown in FIG. 11, the suction plate 45 is provided with through holes 451, through which gas can pass. For example, the through hole 451 is rectangular, rounded rectangular, circular, elliptical, triangular, trapezoidal, square, or other shapes.

Figure 12:
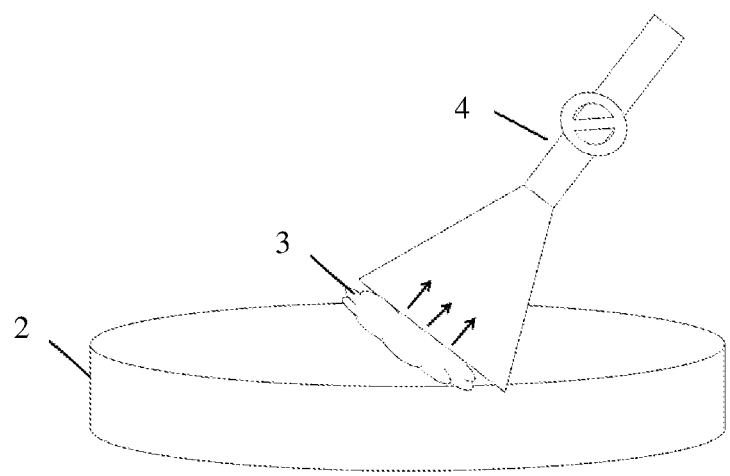
FIG. 12 is a schematic view of a suction process of a cell sheet suction device according to one embodiment of the present disclosure.

FIG. 12 is a schematic view of a suction process of a cell sheet suction device according to one embodiment of the present disclosure. As shown in FIG. 12, after the cell sheet is stripped and blown up by the cell sheet transfer device 1, the cell sheet is suctioned by the cell sheet suction device 4.

Figure 13:
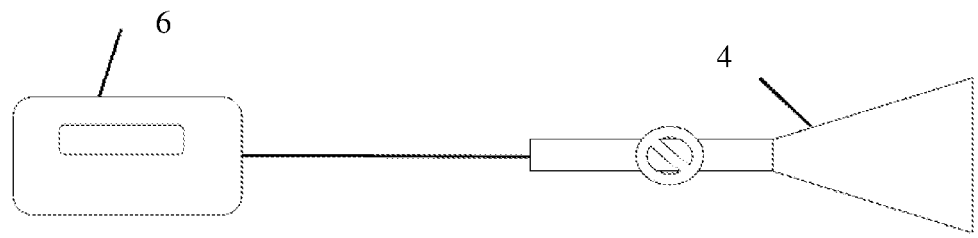
FIG. 13 is a schematic structural view of a cell sheet processing apparatus according to still another embodiment of the present disclosure.
Figure 13:
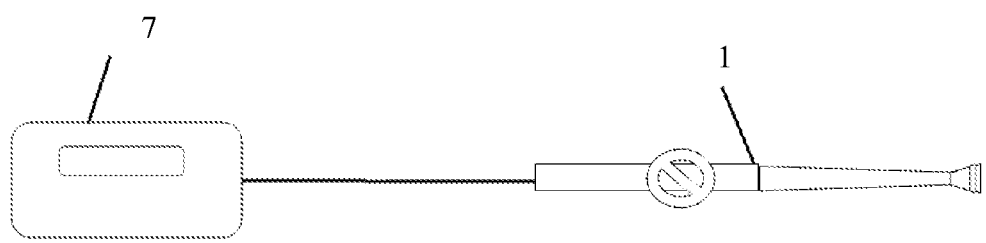

FIG. 13 is a schematic structural diagram of a cell sheet processing apparatus according to still another embodiment of the present disclosure. As shown in FIG. 13, the cell sheet processing apparatus includes a first pressure source 7 and a second pressure source 6 in addition to the cell sheet transfer device 1 and the cell sheet suction device 4.

The first pressure source 7 communicates with the first tubular body of the cell sheet transfer device 1 through a pipeline, such that the cell sheet can be stripped and blown up by the cell sheet transfer device 1. The second pressure source 6 communicates with the connecting tube of the cell sheet suction device 4 through a pipeline, such that the cell sheet can be suctioned by the cell sheet suction device 4.

In some embodiments, the first pressure source 7 is a positive pressure source and the second pressure source 6 is a negative pressure source.

Figure 14:
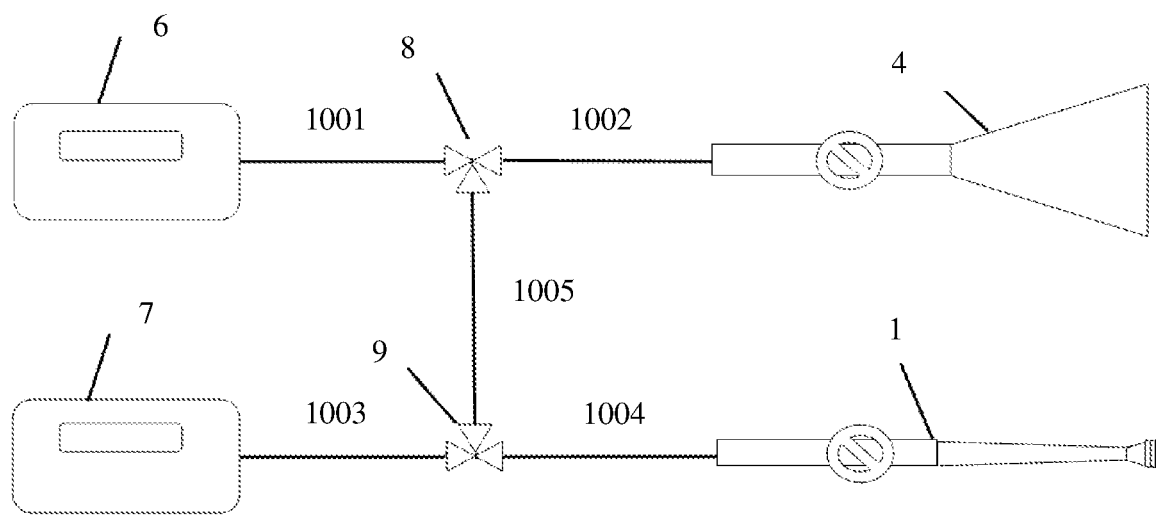
FIG. 14 is a schematic structural diagram of a cell sheet processing apparatus according to still another embodiment of the present disclosure.

FIG. 14 is a schematic structural diagram of a cell sheet processing apparatus according to still another embodiment of the present disclosure. As shown in FIG. 14, a first three-way valve 9 is disposed between the first pressure source 7 and the cell sheet transfer device 1, and a second three-way valve 8 is disposed between the second pressure source 6 and the cell sheet suction device 4.

The first pressure source 7 communicates with a first end of the first three-way valve 9 through a pipeline 1003, and the cell sheet transfer device 1 communicates with a second end of the first three-way valve 9 through a pipeline 1004, and a third end of the first three-way valve 9 communicates with a third end of a second three-way valve 8 through a pipeline 1005. The second pressure source 6 communicates with a first end of a second three-way valve 8 through a pipeline 1001, and the cell sheet suction device 4 communicates with a second end of the second three-way valve 8 through a pipeline 1002.

Through the above connection, the wind blown by the first pressure source 7 can reach the second pressure source 6 through the pipelines 1003, 1005 and 1001, thereby enhancing the suction force of the cell sheet suction apparatus 4.

Thus far, various embodiments of the present disclosure have been described in detail. Some details well known in the art have not been described in order to avoid obscuring the concepts of the present disclosure. Those skilled in the art can now fully appreciate how to implement the teachings disclosed herein, in view of the foregoing description.

Although some specific embodiments of the present disclosure have been described in detail by way of example, it should be understood by those skilled in the art that the above examples are for illustration only and are not intended to limit the scope of the present disclosure. It will be understood by those skilled in the art that various changes may be made and equivalents may be substituted for elements thereof without departing from the scope and spirit of the present disclosure. The scope of the present disclosure is defined by the appended claims.

What is claimed is:
1. A cell sheet processing apparatus, comprising:
 a cell sheet transfer device, the cell sheet transfer device comprising:
 a first tubular body;

a second tubular body disposed at an end of the first tubular body and communicating with the first tubular body;

a cell shovel disposed at the end of the first tubular body and disposed on one side of the second tubular body, wherein a free end of the cell shovel exceeds a free end of the second tubular body; and a waterproof and air-permeable membrane disposed in the first tubular body and configured to prevent the cell sheet from entering an inner part of the first tubular body, thereby preventing the cell sheet from being contaminated in the inner part of the first tubular body; and a cell sheet suction device, comprising:

a connection tube; and a suction member disposed at an end of the connection tube and configured to communicate with the connecting tube to suction the cell sheet.

2. The cell sheet processing apparatus according to claim 1, wherein the cell sheet transfer device further comprising:

a filter membrane holder disposed in the first tubular and configured to secure the filter membrane.

3. The cell sheet processing apparatus of claim 1, wherein a cross-sectional area of the second tubular body increases gradually in a direction from a connection end of the second tubular body and the first tubular body toward the free end of the second tubular body.

4. The cell sheet processing apparatus of claim 1, wherein the first tubular body comprises a bending section.

5. The cell sheet processing apparatus of claim 4, wherein a bending angle of the bending section is from 30 degrees to 60 degrees.

6. The cell sheet processing apparatus of claim 1, wherein the cell sheet transfer device an further comprising:

a pressure regulator disposed on the first tubular body and configured to regulate pressure inside the first tubular body.

7. The cell sheet processing apparatus according to claim 1, wherein a material of the first tubular body and a material of the second tubular body are high histocompatibility materials.

8. The cell sheet processing apparatus according to claim 7, wherein the high histocompatibility material comprises at least one of polyethylene, polypropylene, polyethylene glycol, polystyrene, nylon, polyacetal, polycarbonate, polyvinyl alcohol, polyethyleneimine, polysulfone, polylactic acid, polymethacrylate, polyurethane, glass, ceramic, or dextran.

9. The cell sheet processing apparatus according to claim 1, wherein a cross-sectional area of the suction member increases gradually in a direction from a connection end of the suction member and the connection tube to a free end of the suction member.

10. The cell sheet processing apparatus according to claim 1, wherein the cell sheet suction device further comprises:

a pressure regulator disposed on the connection tube and configured to regulate pressure inside the connection tube.

11. The cell sheet processing apparatus according to claim 1, wherein the cell sheet suction device further comprises a filter membrane disposed in the suction member.

12. The cell sheet processing apparatus according to claim 11, wherein the cell sheet suction device further comprises:

a suction plate disposed on one side of the free end of the filter membrane close to the suction member.

13. The cell sheet processing apparatus according to claim 12, wherein the suction plate is provided with through holes.

14. The cell sheet processing apparatus according to claim 1, further comprising:

a first pressure source configured to communicate with the first tubular body of the cell sheet transfer device through a first pipeline to make the cell sheet transfer device blow up the cell sheet; and a second pressure source configured to communicate with the connection tube of the cell sheet suction device through a second pipeline to make the cell sheet suction device to suction the cell sheet.

15. A cell sheet processing apparatus according to claim 14, further comprising:

a first three-way valve disposed on the first pipeline; and a second three-way valve disposed on the second pipeline.

* * * * *